United States Patent [19]

Schmid et al.

[11] Patent Number: 5,733,364

[45] Date of Patent: Mar. 31, 1998

[54] GONIOCHROMATIC LUSTER PIGMENTS WITH ALUMINUM COATING

[75] Inventors: Raimund Schmid, Neustadt; Norbert Mronga, Dossenheim; Jörg Adel, Ludwigshafen, all of Germany

[73] Assignee: BASF Aktiengesellschaft, Ludwigshafen, Germany

[21] Appl. No.: 637,470

[22] Filed: Apr. 25, 1996

[30] Foreign Application Priority Data

May 3, 1995 [DE] Germany ................. 195 16 181.5

[51] Int. Cl.$^6$ ................................... C09C 1/62
[52] U.S. Cl. ............... 106/403; 106/404; 106/415; 106/417; 106/418; 106/442; 106/446; 106/450; 106/454
[58] Field of Search ................. 106/415, 417, 106/418, 403, 404, 454, 442, 446, 450

[56] References Cited

U.S. PATENT DOCUMENTS

| | | | |
|---|---|---|---|
| 3,438,796 | 4/1969 | Hanke | 106/403 |
| 3,639,139 | 2/1972 | Schneggenburger et al. | 427/256 |
| 4,923,717 | 5/1990 | Gladfelter et al. | 427/255.7 |
| 5,151,305 | 9/1992 | Matsumoto et al. | 427/255.7 |
| 5,217,756 | 6/1993 | Shinzawa | 425/252 |
| 5,277,711 | 1/1994 | Schmidt et al. | 106/418 |
| 5,352,286 | 10/1994 | Schmid et al. | 106/404 |
| 5,505,991 | 4/1996 | Schmid et al. | 427/215 |
| 5,607,504 | 3/1997 | Schmid et al. | 106/403 |

FOREIGN PATENT DOCUMENTS

| | | |
|---|---|---|
| 0 033 457 | 8/1981 | European Pat. Off. . |
| 0 045 851 | 2/1982 | European Pat. Off. . |
| 0 338 428 | 10/1989 | European Pat. Off. . |
| 0 571 836 | 12/1993 | European Pat. Off. . |
| 0 668 329 | 8/1995 | European Pat. Off. . |
| 0 686 675 | 12/1995 | European Pat. Off. . |
| 0 708 155 | 4/1996 | European Pat. Off. . |
| 42 23 384 | 1/1994 | Germany . |
| 43 13 541 | 10/1994 | Germany . |
| 43 40 141 | 6/1995 | Germany . |
| 44 05 492 | 8/1995 | Germany . |
| 44 14 079 | 10/1995 | Germany . |
| 44 19 173 | 12/1995 | Germany . |

*Primary Examiner*—Mark L. Bell
*Assistant Examiner*—Scott L. Hertzog
*Attorney, Agent, or Firm*—Oblon, Spivak, McClelland, Maier & Neustadt, P.C.

[57] ABSTRACT

Goniochromatic luster pigments based on multiply coated platelet-shaped metallic substrates comprising at least one layer packet of A) a layer consisting essentially of silicon oxide, silicon oxide hydrate, aluminum oxide and/or aluminum oxide hydrate, and B) a metallic layer which consists essentially of aluminum and is at least partially transparent to visible light, and also, if desired, additionally C) an outer layer which consists essentially of colorless or selectively absorbing metal oxide and/or is phosphate-, chromate- and/or vanadate-containing, are useful for coloring paints, inks, including printing inks, plastics, glasses, ceramic products and decorative cosmetic preparations.

10 Claims, No Drawings

GONIOCHROMATIC LUSTER PIGMENTS WITH ALUMINUM COATING

The present invention relates to novel goniochromatic luster pigments based on multiply coated platelet-shaped metallic substrates comprising at least one layer packet of A) a layer consisting essentially of silicon oxide, silicon oxide hydrate, aluminum oxide and/or aluminum oxide hydrate, and B) a metallic layer which consists essentially of aluminum and is at least partially transparent to visible light, and also, if desired, additionally C) an outer layer which consists essentially of colorless or selectively absorbing metal oxide and/or is phosphate-, chromate- and/or vanadate-containing.

The invention further relates to mixtures of pigments (I) and multiply coated silicatic platelets (II) comprising A') a layer consisting essentially of colorless or selectively absorbing metal oxide, B') a metallic layer which consists essentially of aluminum and is at least partially transparent to visible light, and if desired C') an outer layer which consists essentially of colorless or selectively absorbing metal oxide and/or is phosphate-, chromate- and/or vanadate-containing, as essential components.

The invention also relates to the production of the goniochromatic luster pigments and to their use for coloring paints, inks, including printing inks, plastics, glasses, ceramic products and decorative cosmetic preparations.

Luster effect pigments are used in many sectors of industry, for example in automotive coatings, decorative coating, plastics pigmentation, paints, printing inks, especially security printing inks, and cosmetics.

Their optical effect is based on the directed reflection of light at predominantly sheetlike, mutually parallel-oriented, metallic or strongly refractive pigment particles. Depending on the composition of the pigment platelets, interference, reflection and absorption phenomena create angle-dependent color and lightness effects.

Owing to their uncopyable optical effects, these pigments are increasingly gaining in importance for the production of forgeryproof security documents, such as banknotes, checks, check cards, credit cards, tax stamps, postage stamps, rail and air tickets, telephone cards, lottery tickets, gift vouchers, passes and identity cards.

Markings prepared with the luster effect pigments and the absence of these markings or their alteration, for example in a color copy (disappearance of color flops and luster effects), are safely discernible by the unaided, naked eye and so make it easy to distinguish the original from the copy.

Metallic substrate luster pigments, having high hiding power, are also of particular interest for automotive coatings.

Hitherto the metallic substrate luster pigments used for this purpose have been iron oxide-coated aluminum pigments, as described in EP-A-33 457, which exhibit strong golden to red reflection colors at the specular angle, but look achromatic at steeper viewing angles. To obtain coatings with a two-tone effect, these pigments are therefore mixed with color pigments of a different color.

Goniochromatic pigments, which exhibit an angle-dependent color change between different interference colors, ie. bring about a two-tone effect in coatings or prints even without other pigments, are known from, for example, U.S. Pat. No. 3,438,796, which describes symmetrically constructed pigments consisting of a central opaque aluminum film (60 nm in thickness) coated on both sides with a thick $SiO_2$ film (500 nm), a transparent aluminum film (20 nm), and a thin $SiO_2$ film (200 nm).

These pigments are produced by coating a substrate film alternately with $SiO_2$ and with aluminum vapors in a high vacuum. The multilayered film deposited in this manner is then removed from the substrate film, for example by scratching it off, and comminuted to particle sizes typical of luster pigments (about 5–50 μm).

Owing to the manner of manufacture, the central metal film of these pigments is coated only on the platelet top and bottom and is therefore only incompletely protected from the environment or the attack of chemicals. In addition, the manufacturing process is also very complicated and costly.

German Patent Applications P 44 05 492.0 and P 44 19 173.1 disclose goniochromatic luster pigments where aluminum platelets which in the case of P 44 19 173.1 have been coated with an inner ferromagnetic layer and are therefore magnetizable, are initially coated wet-chemically with silicon oxide by hydrolytic decomposition of organosilicon compounds and subsequently with metallic layers by chemical vapor deposition (CVD). German Patent Application P 44 37 752.5 discloses a CVD process whereby the $SiO_2$ layer can also be applied by gas phase decomposition of organosilicons. Luster pigments comprising aluminum coatings, however, are not described.

It is an object of the present invention to provide goniochromatic luster pigments which are free of the disadvantages mentioned and have advantageous application properties.

We have found that this object is achieved by the above-described luster pigments and their mixtures with multiply coated silicatic platelets.

We have also found a process for producing these luster pigments, which comprises coating the metallic substrate platelets with layers (A) by gas phase decomposition of volatile organosilicons using water vapor and/or oxygen or by hydrolytic decomposition of organic silicon or aluminum compounds in which the organic radicals are attached to the metal via oxygen atoms in the presence of an organic solvent in which the metal compounds are soluble and subsequent drying, metallic layers (B) by gas phase decomposition of volatile aluminum alkyls or trialkylamine adducts of aluminum hydride in an inert atmosphere and if desired layer (C) by gas phase decomposition of volatile metal or phosphorus compounds in the presence of oxygen and/or water vapor.

Finally, the present invention also provides for the use of these luster pigments and luster pigment mixtures for coloring paints, inks, including printing inks, plastics, glasses, ceramic products and decorative cosmetic preparations.

Suitable metallic substrates for the luster pigments of the present invention include all metals and alloys in platelet form known for metallic effect pigments. Examples besides steel, copper and its alloys such as brass and bronzes include in particular aluminum and its alloys such as aluminum bronze.

Preference is given to aluminum flakes which are producible in a simple manner by the stamping out of aluminum foil or by common atomizing and grinding techniques.

Suitable aluminum platelets are produced for example by the Hall process by wet grinding in white spirit. The starting material is an atomized, irregular aluminum grit which is ball-milled in white spirit and in the presence of lubricant into platelet-shaped particles and subsequently classified.

Commercial products can be used. However, the surface of the aluminum particles should be substantially free of fats or other coating media. These substances can to some extent be removed by solvent treatment or better, as described in DE-A-42 23 384, by oxidative treatment.

Furthermore, the metallic substrate particles may have been given a passivating treatment, ie. may have been given a coating which confers resistance especially against water, as known for example from DE-A-42 36 332 and German Patent Application P 44 14 079.7.

The term "passivating coatings" also encompasses metal oxide layers. Examples of further suitable substrates are therefore iron oxide-coated metal pigments (eg. EP-A-33 457) having a (weak) golden to red self-color and delicately pastel-colored titania-coated metal pigments (eg. EP-A-338 428). However, the metal oxide layer should not be too thick in order that the substrate particles may retain their "metallic coloristics".

Other suitable substrate materials are finally magnetizable aluminum platelets which comprise a ferromagnetic, iron-, cobalt-, nickel-, magnetite- or $\gamma$-$Fe_2O_3$-containing coating (DE-A-43 13 541 and German Patent Applications P 43 40 141.4 and P 44 19 173.1) and make it possible to produce magnetizable goniochromatic luster pigments.

The size of the substrate particles is not critical per se and can be adapted to the particular use. In general, the particles have average largest diameters from about 1 to 200 µm, in particular from about 5 to 100 µm, and thicknesses from about 0.1 to 5 µm, in particular round about 0.5 µm. Their specific free surface area (BET) is generally within the range from 0.1 to 5 $m^2/g$.

The luster pigments of the present invention have a multiple coating on the metallic substrate.

Layer (A) includes as essential constituents aluminum oxide, aluminum oxide hydrate and preferably silicon oxide and silicon oxide hydrate and also mixtures thereof.

The thickness of the layer (A) is generally within the range from 20 to 800 nm, preferably within the range from 50 to 600 nm. Since layer (A) essentially determines the hue of the pigments of the present invention, it has a minimum thickness of about 100 nm for the preferred luster pigments which have only a layer packet (A)+(B) and a particularly pronounced color play.

As the thickness of layer (A) increases, in the case of pigments coated with layer (A) and metallic layer (B) an observer at a viewing angle of 25° will see interference color changing repeatedly in succession from blue to green to gold to red. The angle dependence of the hue increases from the first interference color series to higher series (ie. to thicker layers (A)). For instance, a reddish gold of the first series will flop as a function of the angle into a greenish gold, while such hue in the second or third interference series will flop toward the complementary color, a greenish blue.

Layer (B), consisting essentially of metallic aluminum, should be at least partially transparent (semitransparent) to visible light and therefore generally has a thickness from 1 to 25 nm, preferably from 5 to 20 nm.

If a plurality (eg. 2, 3 or 4) of layer packets (A)+(B) are present, then layer (A) is preferably from 20 to 400 nm and layer (B) is preferably from 2 to 5 nm in thickness. However, preference is given to luster pigments having only a layer packet of (A)+(B).

The luster pigments of the present invention may further include an outer layer (C), in particular for protecting aluminum layer (B) underneath.

Layer (C) can be constructed from low refractive index or high refractive index metal oxides which can be not only colorless but also selectively absorbing. Examples of suitable metal oxides include silicon oxide, silicon oxide hydrate, aluminum oxide, aluminum oxide hydrate, tin oxide, titanium dioxide, zirconium oxide, iron(III) oxide and chromium(III) oxide, preference being given to silicon oxide in particular aluminum oxide which can be formed with advantage by surface oxidation of the aluminum surface of layer (B).

Layer (C), however, can also be a phosphate-, chromate- and/or vanadate-containing or else phosphate- and $SiO_2$-containing layer to be obtained by gas phase passivation (DE-A-42 36 332 and German Patent Application P 44 14 079.7), which also makes it possible in particular to use the luster pigments of the present invention in waterborne coatings or other aqueous systems.

The thickness of layer (C) is generally from about 1 to 400 nm, preferably from 5 to 250 nm. For example, when layer (C) is an $SiO_2$ layer it preferably has a thickness from 50 to 250 nm and if it is an $Al_2O_3$ layer formed by surface oxidation of aluminum layer (B) or a phosphate- and optionally $SiO_2$-containing passivating layer (c) it preferably has a thickness from 5 to 20 nm.

Of course, layer (C) may likewise contribute to the interference color of the pigment and continue the interference color series at the point determined by the substrate coated with (A) and (B). This is the case, for example, when zirconium oxide or titanium oxide is applied as layer (C). If, in contrast, layer (C) consists essentially of silicon oxide, this layer will hardly be coloristically noticeable in the application medium (eg. paints or inks) which has a similar refractive index.

Finally, colored metal oxides such as iron oxide and chromium oxide will with their absorption color modify, and with increasing thickness ultimately obscure, the interference color of the multilayer system.

In the luster pigments of the present invention, all layers are altogether noticeable for their uniform, homogeneous and filmlike construction and their interference capability even at relatively high thicknesses, resulting in strong interference color multilayer systems in which the substrate particles are coated on all sides, not only on the upper and lower surface of the platelet.

Coloristically, mixtures of the novel metallic pigments (I) with likewise multiply coated silicatic platelets (II) are also of particular interest.

Suitable silicatic substrates are, in particular light-colored and white micas, and flakes of preferably wet-ground muscovite are particularly preferred. Of course, it is also possible to use other natural micas such as phlogopite and biotite, artificial micas, and talc and glass flakes.

The silicatic substrate particles used have a metal oxide layer (A') which is preferably constructed from high refractive metal oxides such as titanium oxide, zirconium oxide, zinc oxide, tin oxide, chromium oxide, iron oxide and/or bismuth oxychloride. Aluminum oxide and silicon oxide may likewise be present.

Particular preference is given to mica pigments comprising a layer (A') which consists essentially of titanium dioxide and includes the other oxides mentioned at most in a minor amount.

Metal oxide-coated silicatic pigments are generally known and are also commercially available under the designations of Iriodin® (Merck, Darmstadt), Flonac® (Kemira Oy, Pori) or Mearlin® (Mearl Corporation, New York).

Suitable choice of the silicatic pigments (II) will vary or complement the color play of the metal pigments (I).

If, for instance, a metallic substrate coated with (A) and (B) has a golden hue at a viewing angle of 25°, this golden hue can be shifted toward a more reddish hue by mixing the metal pigment coated only with (A) with titania-coated mica pigments having a reddish golden interference color and subsequent conjoint coating with (B).

The composition of the luster pigment mixtures of the present invention is determined by the desired coloristics.

In principle the weight ratio of metallic pigment (I): silicatic pigment (II) can be varied within the range from 1:99 to 99:1. To obtain adequate hiding power, the pigment mixtures of the present invention preferably include at least 5% by weight of metallic luster pigment (I).

The preferred way of producing the pigment mixtures of the present invention is the conjoint coating of the substrate particles already coated with layer (A) and a layer (A') in the course of step (a) with the metallic layer (B) and if desired the cover layer (C).

Of course, however, all layers can be applied separately and the coated pigments can then be mixed afterwards. This procedure provides the additional option of variation of layers (B) and (B') and also (C) and (C').

In the novel process for producing the luster pigments of the present invention, the individual layers are applied by gas phase decomposition of suitable volatile metal compounds (chemical vapor deposition, CVD) or wet-chemically by hydrolytic decomposition of especially organic metal compounds.

Of course, the two methods can be combined in any desired way for producing the individual layers.

The silicon and/or aluminum oxide layers (A) are equally producible using the wet-chemical method and the CVD method, but the CVD method will usually be preferable, since the aluminum layers (B) are deposited from the gas phase according to the invention. In that case there is no need for intermediately isolating and drying the pigment coated with (A).

In the wet-chemical process described in German Patent Application P 44 05 492.0, organic silicon and/or aluminum compounds in which the organic radicals are bonded to the metals via oxygen atoms are hydrolyzed in the presence of the substrate particles and of an organic solvent in which the metal compounds are soluble.

A multiplicity of organic solvents are suitable for this; isopropanol is preferred.

Preferred examples of the metallic starting compounds are the acetyl acetonates and especially alkoxides, in particular $C_1$–$C_4$-alkoxides, eg. aluminum triisopropoxide and tetraethoxysilane.

The hydrolysis is preferably carried out in the presence of a base or acid as catalyst. Suitable for this purpose are not only for example alkali metal hydroxide solutions such as sodium hydroxide solution but also, in particular, aqueous ammonia solutions. Suitable acid catalysts include for example phosphoric acid and organic acids such as acetic acid and oxalic acid.

Water has to be present at least in the amount required stoichiometrically for the hydrolysis, but it is preferably present in from 2 to 100 times, especially from 5 to 20 times, the amount.

Based on the amount of water used, the rule is to add from 3 to 40% by volume, preferably from 5 to 30% by volume, of a 25% strength by weight aqueous ammonia solution.

As regards temperature management, it is advantageous to heat the reaction mixture to the reflux temperature step by step over a period from 10 to 48 h. If isopropanol is used as solvent, the mixture is preferably stirred for example initially at 40° C. for from 4 to 20 h, then at 60° C. for from 4 to 20 h and finally at 80° C. for from 2 to 8 h.

Technically, step a) of the production process according to the present invention is advantageously carried out as follows:

Substrate particles, organic solvent, water and catalyst (acid or preferably base, in particular for example an aqueous ammonia solution) are charged initially and the metal compound to be hydrolyzed is added pure or dissolved, for example in the form of a from 30 to 70, preferably from 40 to 60, % strength by volume solution in the organic solvent. If the metal compound is added in one step, the suspension is subsequently heated as described above with stirring. However, the metal compound can also be metered in continuously at elevated temperature, in which case water and ammonia can be included in the initial charge or like-wise continuously metered in. On completion of the coating, the reaction mixture is cooled back down to room temperature.

To prevent agglomeration during the coating operation, the suspension can be subjected to a strong mechanical stress such as pumping, vigorous stirring or the action of ultrasound.

If desired, the coating step can be repeated one or more times.

In the CVD process described in German Patent Application P 44 37 752.2, silanes which contain at least one alkanoyloxy radical are decomposed in the gas phase with water vapor and optionally oxygen in the presence of agitated substrate particles. Suitable silanes for this purpose conform in particular to the formula $$R_a SiX_b Y_c$$

where

R is alkyl, preferably $C_1$–$C_{10}$-alkyl, particularly preferably $C_1$–$C_6$-alkyl, which can be substituted by chlorine, which can be monounsaturated or polyunsaturated and whose carbon chain may be interrupted by one or more imino groups or oxygen atoms in the ether function; phenyl, which can be $C_1$–$C_2$-alkyl-substituted, or hydrogen;

X is alkoxy, preferably $C_1$–$C_6$-alkoxy, particularly preferably $C_4$-alkoxy, especially tert-butoxy;

Y is alkanoyloxy, preferably $C_2$–$C_3$-alkanoyloxy, particularly preferably acetoxy;

a is from 0 to 3, preferably from 0 to 2, particularly preferably 0;

b is from 0 to 3, preferably from 1 to 3, particularly preferably 2;

c is from 1 to 4, preferably from 1 to 3, particularly preferably 2, the sum a+b+c=4 and the radicals R for a>1, the radicals X for b>1 and the radicals Y for c>1 can each be identical or different.

Of particular suitability are those silanes which at temperatures ≦600° C., for technical reasons especially ≦300° C., have a sufficiently high vapor pressure to ensure simple vaporization and are also easy to decompose with water vapor and/or air and are depositable as oxide. Of course, it is also possible to use mixtures of different silanes.

Specific examples of preferred silanes include the following:

tetraacetoxysilane, methoxy-, ethoxy-, propoxy-, isopropoxy-, butoxy-, isobutoxy-, sec-butoxy- and tert-butoxy-triacetoxysilane, dimethoxy-, diethoxy-, dipropoxy-, diisopropoxy-, dibutoxy-, diisobutoxy-, di-sec-butoxy- and di-tert-butoxydiacetoxysilane and trimethoxy-, triethoxy-, tripropoxy-, triisopropoxy-, tributoxy-, triisobutoxy-, tri-sec-butoxy- and tri-tert-butoxy-acetoxysilane and also silanes which contain different alkoxy radicals, eg. methoxyethoxydiacetoxysilane.

Very particular preference is given to di-tert-butoxydiacetoxysilane.

To carry out the CVD process, it is advisable, as is generally the case for CVD processes, to use a fluidized bed reactor as described for example in EP-A-45 851. The substrate particles are heated in the reactor to the desired reaction temperature (generally from 100° to 600° C., preferably from 150 to 300° C.) under fluidization with an inert gas such as nitrogen, and silane and water vapor (and optionally oxygen) are then introduced with the aid of inert carrier gas streams (advantageously part-streams of the fluidizing gas) from upstream vaporizer vessels via separate nozzles.

To obtain homogeneous silicon oxide layers which will completely envelop the substrate particles in the form of a film, the silane concentration is advantageously held at $\leq 5\%$ by volume, preferably $\leq 2\%$ by volume, based on the total amount of gas in the reactor.

The amount of water vapor required for the decomposition depends on the concentration of the silane and should correspond at least to the amount stoichiometrically required for hydrolysis, but preference is given to an amount from 10 to 100 times that amount.

If the silane contains alkyl or phenyl substituents R, it is advisable to have oxygen present in the course of the decomposition if the deposited silicon oxide layer is not to contain carbon residues which generally form when water vapor is used alone.

The substrate particles coated with (A) are coated with aluminum layers (B) in the manufacturing process of the present invention by gas phase decomposition of organoaluminums, in particular aluminum alkyls, or alkylamine adducts of aluminum hydrides.

Of particular suitability for this are volatile aluminum alkyls of the formula

where R is $C_1$–$C_4$-alkyl (methyl, ethyl, propyl, isopropyl, butyl, isobutyl or tert-butyl), X is hydrogen or halogen (fluorine, chlorine, bromine or iodine), a is from 1 to 3, and b is from 0 to 2, and the radicals R can be identical or different in the case of a >1, which also applies to the radicals X when b=2.

As well as monoalkylaluminum hydrides and halides $RAlX_2$, it is advantageous to use dialkylaluminum hydrides and halides $R_2AlX$ such as dimethylaluminum hydride, diethyl aluminum hydride and diisobutylaluminum hydride and in particular aluminum trialkyls such as tripropylaluminum, tributylaluminum, triisobutylaluminum, tri-tert-butylaluminum and especially triethylaluminum and triethylaluminum, which can also be used in the form of mixtures.

Instead of aluminum alkyls it is possible to use tri($C_1$–$C_4$-alkyl)amine adducts of aluminum hydride, especially the mono- and diadducts, for example $AlH_3 \times N(CH_3)_3$, $AlH_3 \times N(C_2H_5)_3$, $AlH_3 \times 2N(CH_3)_3$, $AlH_3 \times 2N(C_2H_5)_3$ and $AlH_2(BH_4) \times 2N(CH_3)_3$.

Aluminum layers (B) are advantageously applied by charging the aluminum alkyl to a vaporizer vessel which is disposed upstream of the coating reactor and which has been heated stepwise to about 100°–150° C., in the form of a solution in a volatile hydrocarbon such as petroleum, transferring the aluminum alkyl by means of an inert gas stream (eg. argon in particular nitrogen) passed through this solution into the reactor, via a preferably temperature-controlled nozzle, and thermally decomposing it in the reactor, generally at from 100° to 500° C., preferably at from 150° to 400° C., thereby depositing an aluminum film on the agitated (A)-coated substrates in the reactor. The quantity of volatile aluminum compound in the gas should generally not exceed more than 2% by volume, preferably not more than 1% by volume, of the total amount of gas in the reactor.

The preferred reactor is in particular the above-mentioned fluidized bed reactor, but it is also possible to use a single-neck round-bottom flask made of quartz glass which is rotated by a motor, provided with gas inlet and outlet lines in the axis of rotation and heated by a clamshell oven.

In principle the reactor used can be any heatable mixer which agitates the substrate particles gently by means of appropriate internal fitments and permits the supply and removal of gas.

For a continuous process on an industrial scale it is also possible to use, for example, a rotary tube furnace to which the substrate particles and the aluminum alkyl/inert gas mixture are fed continuously.

Outer metal oxide layers (C) are applied in the process of the present invention by well known oxidative gas phase decomposition of the metal carbonyls (eg. iron pentacarbonyl, chromium hexacarbonyl) or hydrolytic gas phase decomposition of the metal alkoxides (eg. titanium and zirconium tetra-n- and -isopropoxide) (EP-A-33 457, EP-A-338 428) or by the above-described gas phase hydrolysis of organosilicon.

$Al_2O_3$ layers can advantageously be obtained by controlled oxidation in the course of the otherwise inert gas cooling of the pigments coated with aluminum (B).

An advantageous way of carrying this out is to admit air a little at a time in the course of the cooling, starting at from about 80° to 20° C., and observe the reactor temperature. If relatively thick $Al_2O_3$ layers ($\geq 5$ nm) are to be formed, it is advisable to admit further air, preferably saturated with water vapor, at temperatures from about 100° C. to about 400° C. are the first, surface oxidation.

Here it must be borne in mind that the $Al_2O_3$ layer will grow at the expense of the deposited aluminum film and that it would therefore be necessary to apply thicker aluminum layers from the start than are to be present in the end product.

Phosphate-, chromate- and/or vanadate-containing and also phosphate- and $SiO_2$-containing outer layers (C) can be applied by the passivation processes described in DE-A-42 36 332 and German Patent Application P 44 14 079.7 by hydrolytic or oxidative gas phase decomposition of oxide halides of the metals (eg. $CrO_2Cl_2$, $VOCl_3$), in particular phosphorus oxyhalides (eg. $POCl_3$), phosphoric and phosphorous esters (eg. di- and trimethyl and -ethyl phosphite) and amino-containing organosilicons (eg. 3-aminopropyltriethoxy- and -trimethoxysilane).

Luster pigments which are particularly stable in aqueous systems are obtained from a combined decomposition of the phosphorus and silicon compounds.

The manufacturing process of the present invention provides a simple way of reproducibly producing large amounts of multiply coated luster pigments. The pigment particles obtained are completely enclosed and have individual coatings of high quality (homogeneous, filmlike).

The luster pigments and luster pigment mixtures of the present invention are advantageously useful for many purposes, such as the coloring of plastics, glasses, ceramic products, decorative cosmetic preparations and in particular coatings, especially automotive coatings, and inks, especially security printing inks. All customary printing processes can be employed, for example screen printing, intaglio printing, bronze printing, flexographic printing and offset printing.

The pigments of the present invention are also advantageously useful for these purposes in admixture with transparent and hiding wet, colored and black pigments and also commercial transparent, colored and black luster pigments based on metal oxide-coated mica and metal pigments, platelet-shaped iron oxides, graphite, molybdenum sulfide and platelet-shaped organic pigments.

EXAMPLES

Preparation and application of luster pigments according to the present invention To incorporate the pigments into a paint, 0.4 g in each case of pigment was dispersed in 3.6 g of a mixed-polyester varnish having a solids content of 21% by weight and the mixture was dispersed in a red devil for 2 min. Drawdowns of the pigmented varnishes were knife-coated onto black and white cardboard at a wet film thickness of 160 μm.

To apply the pigments in screen printing, 10 g of pigment were stirred into 90 g of a commercially available binder solution (22.5 g of PVC copolymer Laroflex® MP45, 4.5 g of methoxypropyl acetate, 13.5 g of n-hexyldiglycol, 49.5 g of butylglycol). The screen printing ink thus prepared was applied with a commercially available screen printing machine (screen mesh size from 112 to 150 μm) to coated, titania-coated paper in a thickness of 45 μm and air-dried.

Example 1 a) In a round-bottom flask equipped with reflux condenser and stirrer, 100 g of finely divided aluminum powder (average particle diameter 20 μm) were suspended in 1.5 l of isopropanol. After addition of 400 ml of water and 40 ml of a 25% strength by weight aqueous ammonia solution, the suspension was heated to 65° C. with vigorous stirring. At the same time the metered addition was commenced of a mixture of 600 ml of isopropanol and 600 g of tetraethoxysilane (rate of addition 100 ml/h, 12 h). Following a subsequent stirring time of 10 h and cooling, the product was filtered off, thoroughly washed with isopropanol and dried at 80° C.

The coated aluminum powder had an SiO$_2$ content of 59.3% by weight and a slightly greenish tinge.

b) 200 g of the coated aluminum powder were then heated in a fluidized bed reactor (described in EP-A-571 836) to 200° C. under fluidization with a total of 800 l/h of nitrogen. From an upstream vaporizer filled under argon with 63.5 g of a 20% strength by weight solution of triethylaluminum in petroleum (boiling range 175°14 255° C.), maintained at 50° C. for 2 h and then heated in steps over several hours to 120° C., the triethylaluminum was transferred with a 100 l/h stream of argon through a temperature-controlled nozzle adapted to the vaporizer temperature in the course of about 8 h in total into the reactor and decomposed there to aluminum, ethylene and hydrogen. The reactor was subsequently kept at 200° C. for a further 2 h. In the course of cooling down to room temperature, air was admitted several times in small portions (about 500 ml) to passivate the surface of the deposited aluminum film.

The pigment obtained had an SiO$_2$ content of 58.4% by weight and an aluminum content of in total 41.6% by weight, so that the aluminum coating accounts for 1.5% by weight of the pigment.

On application in a paint and in screen printing, the pigment exhibited strong metallic luster combined with an intensively green interference color which flopped into a reddish blue at steeper viewing angles. A color copy of the screen print produced in a commercial color copier (Canon CLC 500) was free of any angle-dependent color play, only showing a combination shade.

Example 2

Example 1 was repeated with four times the amount of triethylaluminum being decomposed in step b). Owing to the high thickness of the applied aluminum layer, the pigment only exhibited hardly noticeable interference colors. In the course of cooling, the aluminum surface was passivated with air as in Example 1.

Then the fluidizing gases were admixed with a water vapor-saturated air stream, and the reactor was heated to 100° C. in steps. After 5 h the surface oxidation of the aluminum layer had conferred a deep green color on the pigment as in Example 1.

Example 3

Example 1 was repeated with twice the amount of triethylaluminum being decomposed in step b).

On completion of the deposition of aluminum the reactor temperature was lowered to 190° C. Then part of the fluidizing gases (200 l/h) was passed through an upstream vessel containing 25 ml of phosphorus oxychloride temperature-controlled to 40° C. A further 200 l/h of nitrogen transferred additional water vapor into the reactor from a water reservoir temperature-controlled at 50° C. On completion of the POCl$_3$ addition (4 h) the vaporizer reservoir was filled with 20 ml of 3-aminopropyltriethoxysilane and heated at 110° C. and the reactor temperature was raised to 220° C. All the silane had been vaporized after 5 h.

The doubly passivated pigment exhibited an almost unchanged intensive green interference color as in Example 1.

We claim:

1. Goniochromatic luster pigments based on multiply coated platelet-shaped metallic substrates comprising at least one layer packet of A) a layer consisting essentially of silicon oxide, silicon oxide hydrate, aluminum oxide and/or aluminum oxide hydrate, coat on all sides of the substrate and B) further coated on all sides by a metallic layer which consists essentially of aluminum and is at least partially transparent to visible light, and also, if desired, additionally C) an outer layer which consists essentially of colorless or selectively absorbing metal oxide and/or is phosphate-, chromate- and/or vanadate-containing.

2. Luster pigments as claimed in claim 1 wherein the metal oxide of layer (C) is silicon oxide, silicon oxide hydrate, aluminum oxide, aluminum oxide hydrate, titanium dioxide, zirconium dioxide, iron(III) oxide and/or chromium (III) oxide.

3. Luster pigments as claimed in claim 1 comprising only one layer packet (A)+(B).

4. Luster pigments as claimed in claim 1 wherein the metallic substrate consists essentially of aluminum platelets produced by common atomizing and grinding techniques.

5. Luster pigments as claimed in claim 1 wherein the metallic substrate consists essentially of aluminum platelets coated and/or passivated with a ferromagnetic layer.

6. Luster pigment mixtures of
I) the luster pigments of claim 1, and
II) multiply coated silicatic platelets comprising
   A') a layer consisting essentially of colorless or selectively absorbing metal oxide,
   B') a metallic layer which consists essentially of aluminum and is at least partially transparent to visible light, and if desired
   C') an outer layer which consists essentially of colorless or selectively absorbing metal oxide and/or is phosphate-, chromate- and/or vanadate-containing.

7. A process for producing luster pigments as claimed in claim 1, which comprises coating the metallic substrate platelets with
   layers (A) by gas phase decomposition of volatile organosilicons using water vapor and/or oxygen or by hydrolytic decomposition of organic silicon or aluminum compounds in which the organic radicals are attached to the metal via oxygen atoms in the presence of an organic solvent in which the metal compounds are soluble and subsequent drying,
   metallic layers (B) by gas phase decomposition of volatile aluminum alkyls or trialkyl amine adducts of aluminum hydride in an inert atmosphere and if desired
   layer (C) by gas phase decomposition of volatile metal or phosphorus compounds in the presence of oxygen and/or water vapor.

8. A process for producing luster pigments as claimed in claim 1, which comprises a step of decomposing vaporized aluminum alkyls or trialkylamine adducts of aluminum hydride in an inert atmosphere in the presence of pigment platelets.

9. A process as claimed in claim 8 wherein aluminum alkyls of the general formula $$R_a AlX_b$$

where R is identical or different $C_1$–$C_4$-alkyl, X is hydrogen or halogen, a is from 1 to 3, and b is from 0 to 2, or tri($C_1$–$C_4$-alkyl)amine adducts of aluminum hydride are decomposed.

10. A method for coloring, which comprises adding the luster pigments of claim 1 to paints, inks, plastics, glasses, ceramic products or decorative cosmetic preparations.

* * * * *